US008668727B2

(12) United States Patent
Natale et al.

(10) Patent No.: US 8,668,727 B2
(45) Date of Patent: Mar. 11, 2014

(54) SYSTEMS AND METHODS FOR TREATING PATHOGENIC INFECTION (76) Inventors: Anthony Natale, New Preston, CT (US); David Muller, Boston, MA (US)

(*) Notice: Subject to any disclaimer, the term of this patent is extended or adjusted under 35 U.S.C. 154(b) by 0 days.

(21) Appl. No.: 13/592,883

(22) Filed: Aug. 23, 2012

(65) Prior Publication Data

US 2013/0072852 A1 Mar. 21, 2013

Related U.S. Application Data (60) Provisional application No. 61/526,346, filed on Aug. 23, 2011.

(51) Int. Cl.
*A61N 5/06* (2006.01)
(52) U.S. Cl.
USPC .............................. 607/88; 604/24
(58) Field of Classification Search
USPC .............................. 607/88; 604/24
See application file for complete search history.

(56) References Cited

U.S. PATENT DOCUMENTS

| 5,100,429 | A | 3/1992 | Sinofsky et al. |
| 6,224,893 | B1 | 5/2001 | Langer et al. |
| 7,331,954 | B2* | 2/2008 | Temelkuran et al. ........... 606/15 |
| 2002/0192289 | A1 | 12/2002 | Zheng et al. |
| 2003/0224002 | A1 | 12/2003 | Hasan et al. |
| 2004/0039242 | A1* | 2/2004 | Tolkoff et al. .................... 600/9 |
| 2004/0230156 | A1 | 11/2004 | Schreck et al. |
| 2006/0135644 | A1 | 6/2006 | Engelbrecht et al. |
| 2006/0167531 | A1 | 7/2006 | Gertner et al. |
| 2008/0255549 | A1* | 10/2008 | Rose et al. ....................... 606/15 |
| 2009/0028946 | A1 | 1/2009 | Sheardown et al. |
| 2009/0171305 | A1 | 7/2009 | El Hage |
| 2009/0238778 | A1 | 9/2009 | Mordas et al. |
| 2010/0057060 | A1 | 3/2010 | Herekar |
| 2010/0234793 | A1* | 9/2010 | Dacey et al. ....................... 604/8 |
| 2010/0318017 | A1 | 12/2010 | Lewis et al. |
| 2011/0046441 | A1* | 2/2011 | Wiltshire et al. ............. 600/104 |
| 2011/0060267 | A1 | 3/2011 | DeWoolfson et al. |
| 2011/0085991 | A1 | 4/2011 | Giniger |
| 2011/0190742 | A1 | 8/2011 | Anisimov |
| 2011/0280763 | A1 | 11/2011 | Trokel et al. |
| 2011/0282333 | A1 | 11/2011 | Herekar et al. |
| 2012/0065572 | A1 | 3/2012 | Lewis et al. |
| 2012/0121567 | A1 | 5/2012 | Troisi et al. |

FOREIGN PATENT DOCUMENTS

| EP | 1054642 B1 | 5/2008 |
| EP | 2380535 A1 | 10/2011 |
| WO | WO-0078393 A1 | 12/2000 |
| WO | WO-0167878 A1 | 9/2001 |
| WO | WO-0187416 A1 | 11/2001 |
| WO | WO-03084601 A2 | 10/2003 |
| WO | WO-2007025244 B1 | 12/2007 |

(Continued)

OTHER PUBLICATIONS

International Search Report and Written Opinion mailed Dec. 21, 2012 for International Application No. PCT/US2012/052008 (9 pages).

*Primary Examiner* — Bill Thomson
*Assistant Examiner* — Sebastian X Lukjan
(74) *Attorney, Agent, or Firm* — Bingham McCutchen LLP (57) ABSTRACT

An internal anatomic target that is infected by pathogenic microorganisms is treated using an applicator configured for delivering a therapeutic solution thereto and an UV light-emitting device transmits UV light thereon.

10 Claims, 5 Drawing Sheets

(56) References Cited

FOREIGN PATENT DOCUMENTS

| | | |
|---|---|---|
| WO | WO-2008064904 A1 | 6/2008 |
| WO | WO-2008095148 A3 | 3/2009 |
| WO | WO-2009029049 A8 | 6/2009 |
| WO | WO-2009073213 A1 | 6/2009 |
| WO | WO-2011050164 A1 | 4/2011 |
| WO | WO-2011019940 A3 | 6/2011 |
| WO | WO-2011094758 A2 | 8/2011 |
| WO | WO-2012047307 A1 | 4/2012 |
| WO | WO-2012095876 A1 | 7/2012 |
| WO | WO-2012095877 A1 | 7/2012 |
| WO | WO-2012078980 A3 | 9/2012 |

* cited by examiner

SYSTEMS AND METHODS FOR TREATING PATHOGENIC INFECTION

CROSS-REFERENCE TO RELATED APPLICATION

This application claims priority to and the benefit of, and incorporates herein by reference in its entirety, U.S. Provisional Patent Application No. 61/526,346, which was filed on Aug. 23, 2011.

FIELD OF THE INVENTION

In various embodiments, the present invention relates generally to systems and methods for treating maladies caused by pathogenic microorganisms.

BACKGROUND

Pathogenic microorganisms, including viruses, bacteria, fungi, and protozoans, may cause infections on any bodily surface, either externally on the skin or mucosal surface or internally in the blood or interior tissues.

For example, in otolaryngology, an acute or chronic sinusitis caused by pathogenic microorganisms in the paranasal sinuses is a common problem. Typically, acute bacterial infections are treated using standard antibiotic therapies. Chronic infections, on the other hand, are very difficult to control: a variety of systemic antimicrobial therapies have been proposed to clear such infections, and various surgical therapies are available for removing obstructions to mucosal outflow from the sinuses in order to improve ventilation of the cavities. Despite the large number of existing therapies, however, it is difficult to clear paranasal sinus infections, which often persist due to the presence of biofilms, persistent fluid and mucous collections, poor ventilation, and poor access to systemically delivered therapies.

Acute or chronic otitis media caused by pathogenic microorganisms in the middle ear usually results in a middle ear effusion that impairs hearing ability. Systemic antibiotics have poor penetration into the middle ear cavity and overuse of antibiotics in recurrent otitis media leads to increased antibiotic resistance. Surgical treatment involves placing pressure-equalizing tubes across the tympanic membrane to equalize the pressure in the middle-ear space and provide a channel for drainage of middle-ear effusions. These tubes, however, may also provide a path for pathogenic microorganisms to enter the middle ear cavity from the outside environment, thereby resulting in recurrence of otitis media after the tube placement.

Infections in or around a joint can also be difficult to treat. Joint spaces are typically sterile; orthopedic procedures in which joint spaces are intruded upon and subjected to placement of orthopedic implants may invite post-operative infection. This type of infection leads to serious complications in total joint arthroplasty procedures, for example, that often leads to explantation of the orthopedic implants and/or risk of the patient's health.

Accordingly, these conditions and diseases such as cystitis, periodontal disease, gastritis, vaginosis, esophagitis, colitis, dermatitis, acne, and dental caries remain challenging to treat. Additionally, traditional treatments using systemic antibiotics may provide drug exposure and side effects to areas distant from the site of infection, and are a possible cause of increasing anti-microbial resistance.

One treatment method for reducing infectious pathogens involves adding riboflavin (vitamin B2) to the site of infection or potential infection and exposing the site to ultraviolet (UV) light, which activates the riboflavin. The activated riboflavin chemically alters functional groups of nucleic acids (i.e., DNA and RNA) of the pathogens, thereby interfering with the pathogens' ability to replicate. Such targeted treatments may effectively treat the selected, diseased tissue and solve the difficulties of biofilm formation (in which pathogens form difficult-to-eradicate agglomerations) and subtherapeutic concentrations of systemically delivered antibiotics. These techniques, however, are at present only available for treating pathogenic infections on external anatomic surfaces (e.g., skin and skin structures) or deactivating pathogens in blood products. Additionally, the use of activated riboflavin remains primarily a sterilization technique, not a therapeutic modality. Very few laboratory-based, ex vivo sterilization techniques have in vivo, therapeutic applicability.

Consequently, there is a need for a therapeutic modality that can be applied to pathogen infected regions that are internal to the anatomy and difficult to access therapeutically.

SUMMARY

In various embodiments, the present invention relates to systems and methods for delivering riboflavin to selected anatomical target regions (such as the paranasal sinus cavities, the middle ear, joint spaces, surfaces of orthopedic implants, bladder, oral cavity and dentition, genitourinary tract, or gastrointestinal tract) that are difficult to access and sequentially exposing the target regions to UV light (of a specific wavelength, peak wavelength, or wavelength band) in order to activate the riboflavin and produce an antimicrobial effect. The riboflavin may be applied via any of a variety of delivery vehicles, e.g., as an aqueous solution, as a riboflavin-containing paste, lotion, cream or gel, or as an additive to a rinse solution, toothpaste, or other topical pharmacologic product. Advantages of the present approach include effective reduction of the infectious pathogen without complications or side effects associated with the systemic delivery of antimicrobials, as well as ease of administration by a physician. Additionally, devices in accordance with the present invention are inexpensive and can be easily integrated with surgical instruments.

Accordingly, in one aspect, the invention pertains to a system for treating pathogenic infections. In representative embodiments, the system includes a UV light-emitting device having an emission output and an applicator having a fluid reservoir and a fluid outlet integrated therewith. The emission output and the fluid outlet may be configured for accessing an internal anatomical target and delivering a fluid and UV light thereto. In one implementation, the system includes one or more optical fibers for conducting light from the UV light-emitting device to the emission output.

In various embodiments, the system includes an actuator and a forcing mechanism. The actuator is remotely actuable by a user and configured to (i) cause the forcing mechanism to force a fluid from the fluid reservoir through the fluid outlet and (ii) cause the light-emitting device to emit UV light through the emission output. The actuator may be mechanical (e.g., including a handle and a guide wire). In one embodiment, the system includes a user interface for electronically operating the actuator. The user interface may be, for example, a smartphone, a tablet, or a computer, that communicates wirelessly with the actuator. The user interface may receive and display feedback information from the actuator.

The emission output and the fluid outlet may be formed into a delivery component that is flexible or articulated with an alterable shape to facilitate access to different internal anatomical targets. In some embodiments, the system includes a surgical instrument integrated therewith in a single structure. The system may further include an inflatable balloon proximate to the fluid outlet.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1A:
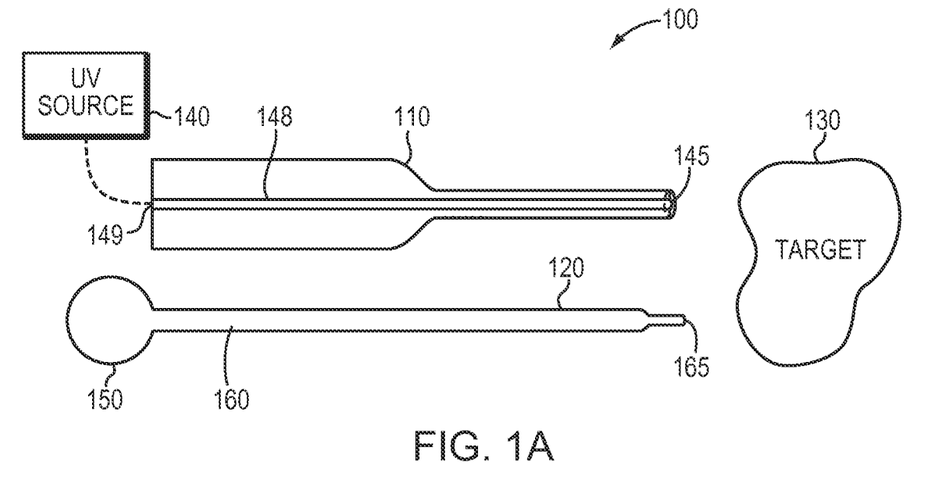
FIG. 1A schematically illustrates a riboflavin solution applicator separate from a UV light-emitting device in accordance with embodiments of the current invention.
Figure 1B:
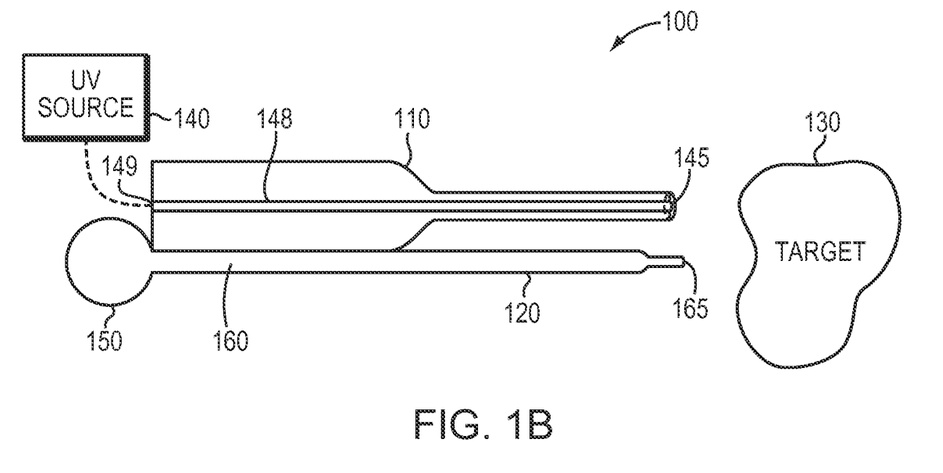
FIGS. 1B and 1C schematically illustrate a riboflavin applicator and a UV light-emitting device combined in a single handheld wand in accordance with embodiments of the current invention.
Figure 1C:
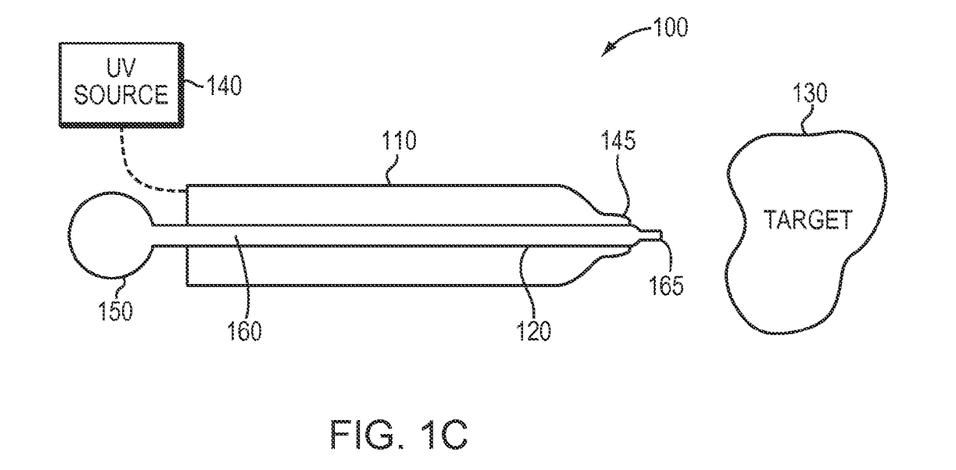

In various embodiments, as illustrated in FIGS. 1A, 1B, and 1C, a system 100 in accordance herewith comprises a UV light-emitting device 110 and an applicator 120 for delivering a riboflavin solution to a target region 130 that is infected by pathogenic microorganisms. The target region 130 is typically an internal anatomic region that is difficult to access. In one embodiment, the riboflavin solution applicator 120 is separate from the UV light-emitting device 110 (FIG. 1A), while in another embodiment, the riboflavin applicator 120 and the UV light-emitting device 110 are combined in a single handheld wand (FIGS. 1B and 1C). The UV light-emitting device 110 is designed to emit a specific wavelength, peak wavelength, or wavelength band (e.g., 340-400 nm) of UV light and to direct the light to the target region 130. In one embodiment, the entire or partial target region that the riboflavin solution is applied thereon is exposed to the emitted UV light. A UV light source 140 that may be located within the UV light-emitting device 110 or may be separate transmits light to the end face 145 of the device 110 via, for example, one or more optical fibers 148. The UV light source is conventional and may be, for example, one or more light-emitting diodes, one or more UV lasers, an incandescent source, etc. The light source 140 may include a suitable power supply (e.g., a battery or circuit that takes power from the AC mains), or may instead include a connector that may be received by a suitable external power supply. Typically the light source 140 will include suitable focusing optics, e.g., for concentrating light onto the proximal end face 149 of an optical fiber 148 for emission at the distal end face 145.

Figure 1D:
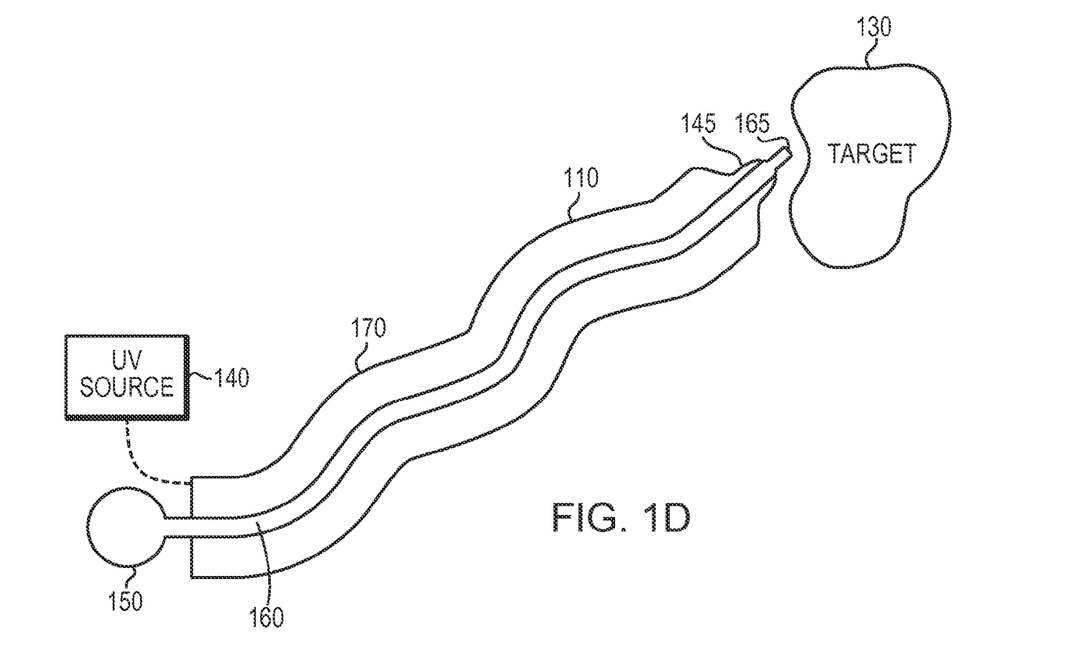
FIG. 1D schematically illustrates delivery ends and/or delivery elements of the UV light-emitting device and the applicator curved or shaped to provide access to the target tissue.

The riboflavin applicator 120 includes a fluid reservoir 150 for storing the riboflavin solution and a delivery element 160 for attaining physical access to the targeted tissue 130 and facilitating delivery of riboflavin thereto. The opening 165 on the tip of the delivery element 160 to the target region 130 may be a simple orifice or the open end of a hollow tube, or may incorporate conventional structures and/or elements for spraying, aerosolizing, misting, and/or causing the riboflavin solution to form small droplets to facilitate delivery over a larger surface area than would be possible with only a simple opening. The delivery ends 145, 165 and/or the delivery elements 170, 160 of the UV light-emitting device 110 and the applicator 120, respectively, may be curved or otherwise shaped in the manner of a surgical instrument (FIG. 1D), and may include a blade, cutter or other access-providing element, which may be retractable. The delivery ends and/or elements may be permanently shaped to facilitate access to a particular anatomic site, or may be formed from a stiff elastic material (e.g., polyurethane or latex) that may be bent by the clinician during use. In some embodiments, the delivery ends and/or elements are made of a shape-memory polymer such as a linear block copolymer of polyurethane, polyethylene terephthalate (PET) or polystyrene, or a thermoplastic material such as polyether ether ketone (PEEK).

Figure 2:
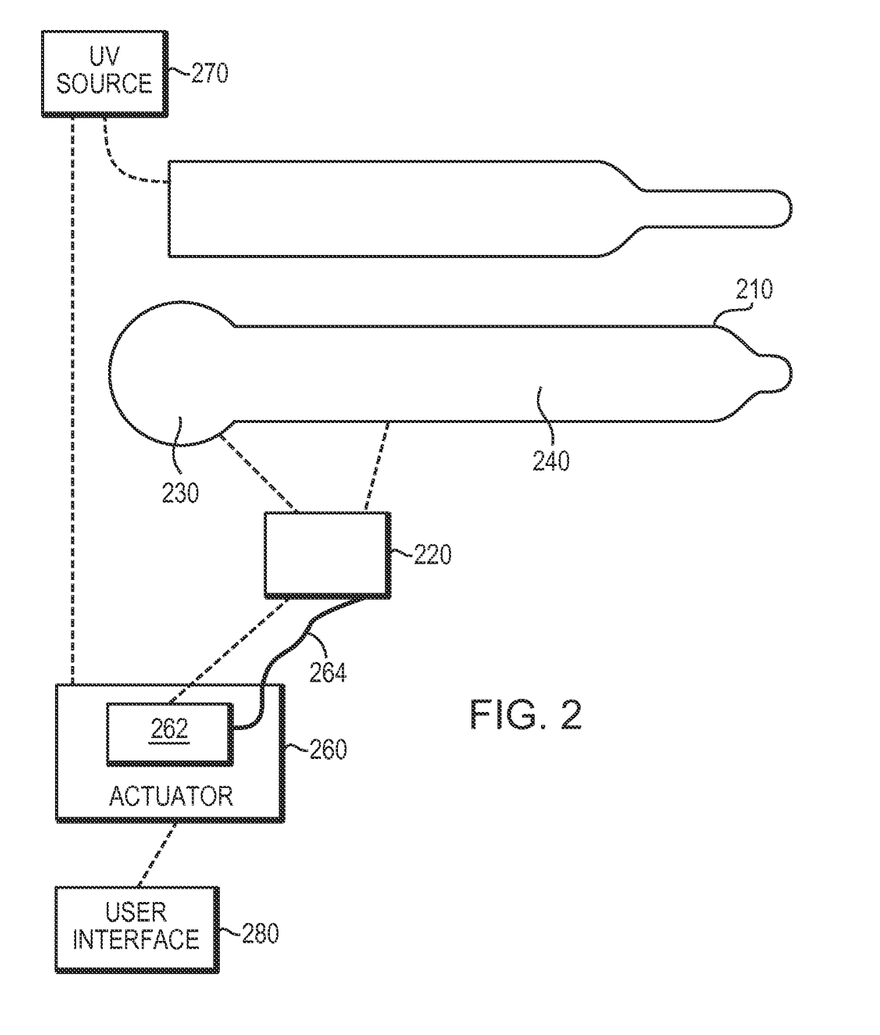
FIG. 2 schematically depicts a mechanical element and/or an actuator incorporated in the UV-activated riboflavin system in accordance with embodiments of the current invention.

Referring to FIG. 2, in various embodiments, the riboflavin solution applicator 210 incorporates a mechanical element 220 for generating pressure to drive the riboflavin solution from the reservoir 230 through the delivery element 240 to the target. The mechanical element may be, for example, a plunger, a pump (e.g., a peristaltic or electrolytic pump), a movable wall or other suitable fluid-driving component. In some embodiments, the mechanical element 220 is operated manually; the user may push a plunger, for example, in the manner of a syringe, or may operate the element 220 remotely via, for example, a stiff guide wire and handle. In other embodiments, a user-controlled actuator 260 directly controls the operation of the mechanical element 220, and the user operates the actuator 260 in a manner that does not require manual movement of a mechanical component.

For example, the actuator 260 may electromechanically or mechanically (e.g., using a handle 262 and a guide wire 264) operate a plunger-type forcing mechanism or electrically operate a pump and/or the UV light source 270. The actuator 260 is typically located on or within the applicator 210, and may be operated by means of a simple button or a more sophisticated user interface 280 that permits the user to specify a volume of riboflavin solution to be administered and/or a rate of administration. The user interface 280 may be part of the applicator 210 or may be remote therefrom, communicating in a wired or wireless manner with the actuator 260 by means of conventional transceiver circuitry. For example, the actuator 260 may be controlled by a computer, a smartphone, a tablet or other wireless devices that transmit signals thereto and, in some embodiments, receive feedback data therefrom.

The applicator 210 may be made of a flexible material or a rigid material, depending on the application. For example, in one embodiment, the applicator is rigid with a preformed shape designed to access a specific target region. In another embodiment, the delivery component 240 is flexible or articulated with an alterable shape that can be manipulated to access different anatomical targets that are difficult to access.

Figure 3A:
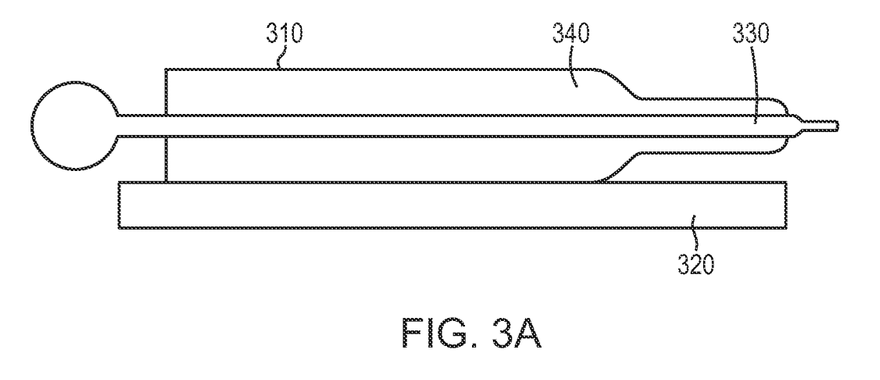
FIG. 3A schematically depicts the UV-activated riboflavin system integrated with a surgical instrument.
Figure 3B:
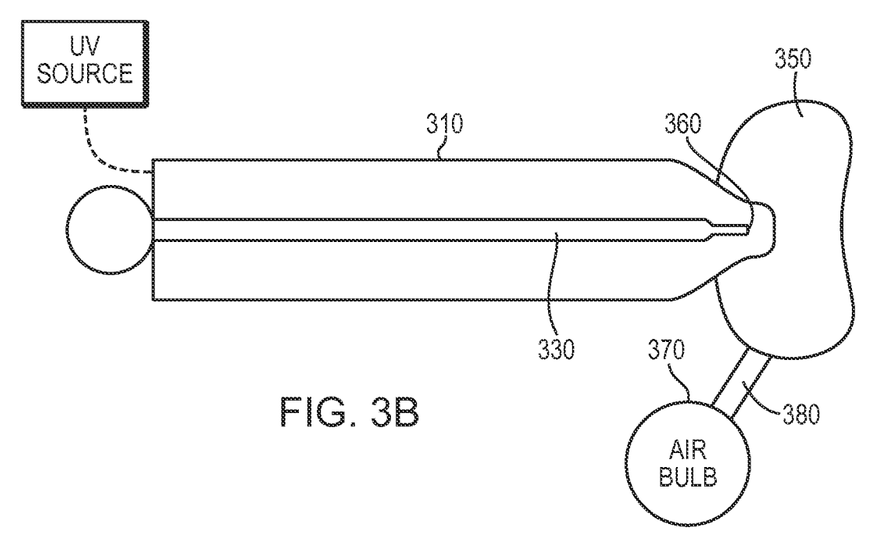
FIG. 3B schematically depicts an inflatable balloon incorporated in the UV-activated riboflavin system to help localize application of the riboflavin.

With reference to FIG. 3A, in some embodiments, the UV-activated riboflavin system 310 is integrated—i.e., attached to or joined to form a single structure—with an existing surgical or interventional instrument 320, e.g., a flexible or rigid endoscope. The endoscope may be, for example, one or more of a cystoscope used in the bladder or urology, a nasopharyngoscope used in the sinuses, nasal cavity, pharynx or ear, nose, and throat (ENT), an arthroscope used, for example, to place or examine orthopedic joints or in other orthopedic applications, a gastrointestinal (GI) endoscope used in the esophagus, stomach, colon, GI tract or gastroenterology generally, a laparoscope used in intrabdominal procedures or other general surgeries, and/or a bronchoscope used in the lungs or pulmonology. The UV light may be channeled through (1) a separate element attached to the endoscope, (2) optical elements of the endoscope itself, or (3) a completely independent optical delivery system resembling a flexible or rigid endoscope with the purpose of emitting UV light. Although the UV-activated riboflavin system 310 and the surgical instrument 320 are depicted in FIG. 3A in the form of a single handheld wand, one of ordinary skill in the art will understand that the riboflavin solution applicator 330 and the UV light-emitting device 340 thereof may be separate, and the surgical instrument 320 may be integrated with either or both of the applicator 330 and the UV light-emitting device 340; for example, the components 330, 340 may separately attach to the body of the instrument 320. The UV light-emitting device 340 may also be combined with, e.g., an articulating shaver to create a combined system for surgical debridement together with the riboflavin and UV light technique. With reference to FIG. 3B, in some embodiments, the UV-activated riboflavin system 310 incorporates a translucent, inflatable balloon 350 to help localize application of the riboflavin and may also be used in connection with related surgical procedures for treating the target region. The inflatable balloon 350 may be positioned adjacent or proximal to the orifice 360 of the riboflavin solution applicator 330. For example, the balloon 350 may surround the system 310 (e.g., inflating to a torus) such that the applicator orifice extends beyond it; in this way, the balloon forms a dam that may completely block the lumen of an anatomical passage, preventing dispersal of the riboflavin solution. In some embodiments, the balloon 350 is inflated using a hand-held air bulb 370, for example, which is fluidly connected to the balloon 350 by a tube 380 running along or within the system 310 or the applicator 330. In other embodiments, the balloon is inflated by command of the actuator 260 (see FIG. 2), which triggers operation of pump. For example, the pump may be the same pump that causes delivery of riboflavin solution through the orifice 360, but selectively channeled to alternately operate the balloon 350 or the fluid-forcing mechanism.

During operation, a riboflavin containing solution may first be applied to a target region; the target region is then exposed to the UV light for a period of time to activate the riboflavin. As further described below, this technique may be carried out as a stand-alone procedure performed in an office or an operating room setting; it may also be performed in conjunction with a variety of other surgical procedures.

Treatment of Paranasal Sinus Cavities

Figure 4A:
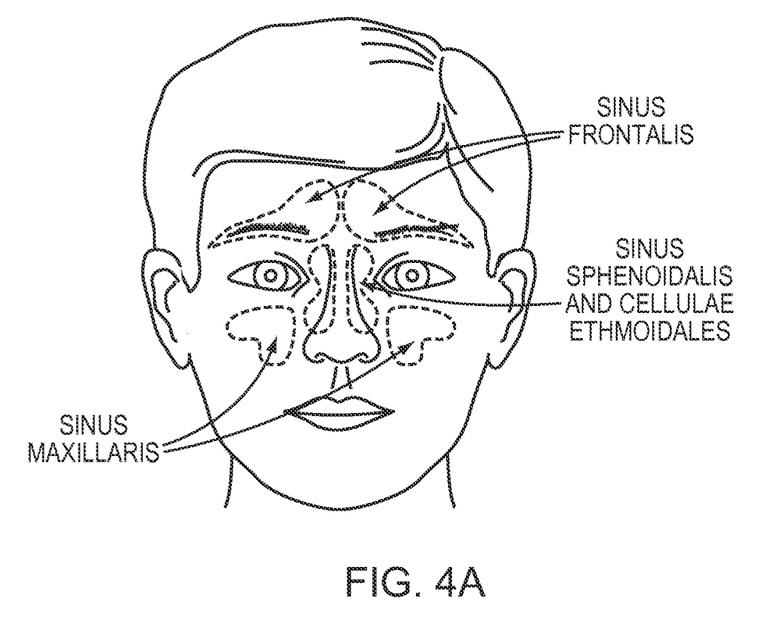
FIG. 4A depicts human paranasal sinus cavities.

Referring to FIG. 4A, the UV-activated riboflavin system may be applied to various paranasal sinus cavities, i.e., sinus maxillaris, sinus frontalis, sinus sphenoidalis, and cellulae ethmoidales or an anatomic area after the sinus has been surgically altered or obliterated. The riboflavin solution applicator 120 first delivers the riboflavin solution to the local target regions (e.g., the paranasal sinus cavity or the walls of the cavity) in individual paranasal sinus cavities. The UV light-emitting device 110 then transmits UV light to activate riboflavin, thereby disturbing proliferation of the pathogens at the target regions. This approach may be performed in connection with a variety of other paranasal sinus procedures, e.g., functional endoscopic sinus surgery, post-surgical debridement of the paranasal sinus cavities and nasal cavity, sinus lavage, balloon sinuplasty, or any combination of such procedures.

Middle Ear Treatments

Figure 4B:
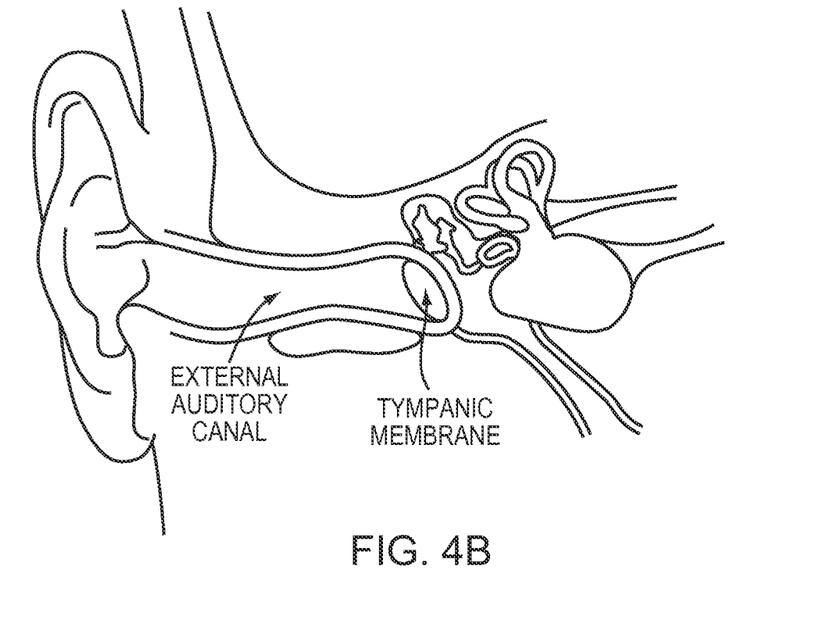
FIG. 4B illustrates the anatomy of a human ear.

Referring to FIG. 4B, in one embodiment, middle-ear infections are treated by delivering riboflavin solution into the middle-ear space through, for example, an existing pressure equalization (PE) tube, followed by emitting UV light across the tympanic membrane (TM). In another embodiment, a transepithelial formulation of riboflavin in the applicator is utilized to deliver the riboflavin solution across the TM without surgical intervention; the TM is then irradiated with UV light at an intensity sufficient for the UV light to cross the membrane and subsequently activate the riboflavin. In another embodiment, the applicator is a catheter that instills riboflavin solution into the middle-ear space. The catheter may include an associated light-delivery element that allows irradiation of the middle-ear space. In still another embodiment, the riboflavin solution is delivered via the applicator directly through an incision in the TM intra-operatively, after which UV light is provided through, for example, an optical fiber inserted across the TM.

Orthopedic Treatments

For orthopedic applications, freshly placed orthopedic implants may be prophylactically treated, or treatment may take place should signs of an infection occur. Prophylaxis is well-suited to total joint arthroplasty, arthroscopic procedures, and debridement of orthopedic joint infections. In various embodiments, the operative field is first flooded with riboflavin solution following implant placement; the field is then irradiated broadly with UV light. Riboflavin solution in the applicator may be, for example, sprayed or aerosolized broadly across the entire operative field to ensure coating of the implant. In one implementation, a riboflavin spraying element is combined with a UV light-delivery element in a single tool. In another embodiment, separate tools are used; for example, the UV light-delivery tool may be capable of irradiating the entire field at once or specific areas of the implant selectively. In still another embodiment, a riboflavin-containing coating is pre-applied to an orthopedic implant and activated by UV light application either intra- or post-operatively.

Dermatologic Treatments

In one embodiment, a riboflavin-containing topical formulation in the applicator is applied to skin or skin structures; a UV light-emitting device is then utilized to irradiate the targeted areas on the skin or skin structures, thereby interfering with the pathogens' ability to proliferate.

Dental Treatments

For dental applications, a riboflavin solution that contains a dental formulation (e.g. toothpaste or oral rinse) may be applied to the dentition or periodontal tissues; a UV light-emitting device configured for oral usage may then be utilized to irradiate the riboflavin applied in the oral cavity and/or on the dental structures for treating the infections.

Gastrointestinal Treatments

To treat gastrointestinal infections, in some embodiments, the applicator delivers the riboflavin solution by incorporation with the working channel of an endoscope. The UV light-emitting device may be configured to transmit UV light via the same working channel, either in conjunction with the UV applicator or as a separate device.

Genitourinary Treatments

In various embodiments, the riboflavin solution is applied to the bladder or urethra via integration of the applicator and a cystoscope. In addition, the UV light is delivered thereto via a UV light emitting element configured for cystoscopic delivery. In some embodiments, a riboflavin formulation is applied intravaginally with a vaginal applicator and the UV light is delivered via an intravaginal light-emitting element.

Accordingly, the present invention provides systems and methods to produce a locally acting antimicrobial effect on the surface that is external or internal to the anatomy and sequentially exposing the riboflavin to UV light. The riboflavin may be applied via use of a riboflavin containing solution, paste, lotion, cream, gel, an additive to a rinse solution, toothpaste, or other topical pharmacologic products. Because this technique can effectively reduce the proliferation rate of infectious pathogens without complications or side effects associated with the systemic delivery of antimicrobials, this technique may be inexpensively and broadly applied to various diseases caused by pathogen infections.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for treating pathogenic infections comprising:
  a UV light-emitting device having an emission output;
  an applicator integrated therewith, the applicator comprising a fluid reservoir for containing a riboflavin solution and a fluid outlet, wherein the emission output and the fluid outlet are configured for accessing an internal anatomical target and delivering the riboflavin solution and UV light thereto;
  an actuator and a forcing mechanism, the actuator being remotely actuable by a user and configured to (i) cause the forcing mechanism to force the riboflavin solution from the fluid reservoir through the fluid outlet and (ii) cause the light-emitting device to emit UV light through the emission output; and
  an inflatable balloon proximal to the fluid outlet;
  wherein the actuator is a mechanical, electrical or electro-mechanical actuator and the applicator is configured to deliver the riboflavin solution through the fluid outlet with the balloon inflated to form a proximal dam preventing dispersal of the fluid.

2. The system of claim 1, wherein the actuator comprises a handle and a guide wire.

3. The system of claim 1, further comprising a user interface for electronically operating the actuator.

4. The system of claim 3, wherein the user interface communicates wirelessly with the actuator.

5. The system of claim 4, wherein the user interface is a smartphone, a tablet, or a computer.

6. The system of claim 4, wherein the user interface receives and displays feedback information from the actuator.

7. The system of claim 1, wherein the emission output and the fluid outlet are formed into a delivery component that is flexible or articulated with an alterable shape to facilitate access to different internal anatomical targets.

8. The system of claim 1, further comprising a surgical instrument integrated with the system in a single structure.

9. The system of claim 1, further comprising at least one optical fiber for conducting light from the UV light-emitting device to the emission output.

10. The system of claim 1, wherein the actuator is further configured to alternately operate the balloon and the forcing mechanism.

* * * * *